United States Patent
Harry et al.

(10) Patent No.: US 9,693,728 B2
(45) Date of Patent: Jul. 4, 2017

(54) SYSTEMS AND METHODS FOR MEASURING MECHANICAL PROPERTIES OF DEFORMABLE MATERIALS

(75) Inventors: Jason D. Harry, Rumford, RI (US); Blair A. Barbour, Madison, AL (US); David Scott Ackerson, Easton, MD (US); Francois I. Luks, Barrington, RI (US)

(73) Assignees: LUCIDUX, LLC, Providence, RI (US); PHOTON-X, INC., Kissimmee, FL (US)

( * ) Notice: Subject to any disclaimer, the term of this patent is extended or adjusted under 35 U.S.C. 154(b) by 873 days.

(21) Appl. No.: 13/172,787

(22) Filed: Jun. 29, 2011

(65) Prior Publication Data

US 2011/0319791 A1 Dec. 29, 2011

Related U.S. Application Data

(60) Provisional application No. 61/344,322, filed on Jun. 29, 2010.

(51) Int. Cl.
*A61B 5/00* (2006.01)

(52) U.S. Cl.
CPC ............ *A61B 5/442* (2013.01); *A61B 5/0053* (2013.01); *A61B 5/0064* (2013.01); *A61B 5/4552* (2013.01)

(58) Field of Classification Search
CPC ..... A61B 5/0053; A61B 5/442; A61B 5/0064; A61B 5/4552
USPC .......................... 600/553, 438, 476, 473, 461
See application file for complete search history.

(56) References Cited

U.S. PATENT DOCUMENTS

| | | | |
|---|---|---|---|
| 5,278,776 A | 1/1994 | Fisher | |
| 5,557,261 A | 9/1996 | Barbour | |
| 5,706,815 A | 1/1998 | Sarvazyan et al. | |
| 5,890,095 A | 3/1999 | Barbour | |
| 5,982,583 A * | 11/1999 | Strom .................. | G11B 5/4826 219/121.69 |
| 6,097,477 A | 8/2000 | Sarrafzadeh-Khoee | |
| 6,312,439 B1 * | 11/2001 | Gordon .................. | A61F 9/013 606/166 |
| 6,324,419 B1 | 11/2001 | Guzelsu | |

(Continued)

OTHER PUBLICATIONS

Huang et al., "An optical coherence tomography (OCT)-based air jet indentation system for measuring the mechanical properties of soft tissues," Meas Sci Technol., Jan. 2009, 20(1), pp. 1-11.

(Continued)

*Primary Examiner* — Sean Dougherty
(74) *Attorney, Agent, or Firm* — Cooper Legal Group LLC

(57) ABSTRACT

Systems and methods deform the surface of the material with a probe, such as a mechanical device or a gas/liquid jet, while optically recording in detail the three-dimensional (3D) topography of the resulting surface deformation. The probe effectively applies a forcing function to the material, the attributes of which are known by performing calibrations prior to use or by direct measurement while it is applied. The topography is effectively the system output that is measured as indicative of the underlying mechanical properties of the material. In one application, systems and methods that apply a pressure in-vivo to human tissue and analyze a three-dimensional topography of the resulting surface deformation to identify localized inhomogeneities and anomalies in the human tissue.

16 Claims, 5 Drawing Sheets

(56) References Cited

U.S. PATENT DOCUMENTS

| | | | |
|---|---|---|---|
| 6,671,390 B1 | 12/2003 | Barbour | |
| 6,810,141 B2 | 10/2004 | Barbour | |
| 7,083,611 B2 * | 8/2006 | Lemchen | 606/9 |
| 7,306,563 B2 * | 12/2007 | Huang | 600/500 |
| 7,731,661 B2 | 6/2010 | Salcudean et al. | |
| 7,797,034 B2 | 9/2010 | Rice et al. | |
| 7,905,835 B2 | 3/2011 | Perrey et al. | |
| 8,023,724 B2 | 9/2011 | Barbour | |
| 2002/0181761 A1 | 12/2002 | Barbour | |
| 2003/0149347 A1 * | 8/2003 | Kauffmann | A61B 5/0002 600/310 |
| 2007/0055179 A1 * | 3/2007 | Deem | A61K 41/0028 601/2 |
| 2008/0259276 A1 * | 10/2008 | Roberts | A61B 3/165 351/212 |
| 2010/0062529 A1 * | 3/2010 | Zimmermann | C12M 35/00 435/379 |
| 2010/0238408 A1 * | 9/2010 | Roberts | A61B 3/165 351/212 |
| 2011/0092821 A1 * | 4/2011 | Fournial | A61B 5/0057 600/473 |

OTHER PUBLICATIONS

Ohtsuka, et al.; "Application of a New Tactile Sensor to Thorascoscpic Surgery: Experimental and Clinical Study," University of Tokyo, 1995 (5 pages).

\* cited by examiner

SYSTEMS AND METHODS FOR MEASURING MECHANICAL PROPERTIES OF DEFORMABLE MATERIALS

CROSS REFERENCE TO RELATED APPLICATIONS

This application claims priority to U.S. Provisional Patent Application No. 61/344,322, filed Jun. 29, 2010, the contents of which are incorporated entirely herein by reference.

BACKGROUND OF THE INVENTION

Field of the Invention

The invention relates to systems and methods for determining the properties of materials, and more particularly, to systems and methods that apply a pressure to a material and analyze a three-dimensional topography of the resulting surface deformation to determine mechanical properties of the material. The invention also relates to systems and methods that apply a pressure in-vivo to human tissue and analyze a three-dimensional topography of the resulting surface deformation to identify localized inhomogeneities and anomalies in the human tissue.

Description of Related Art

It is often desirable to know the mechanical properties (e.g., stiffness, hardness, viscoelasticity, directional anisotropy) of materials. Both quasistatic and dynamic aspects of these properties are of interest. Such materials may be man-made (e.g., metal, plastic, fabric) or natural (e.g., human tissues, animal tissues, plant matter). Sometimes a determination of the bulk average of a mechanical property is sought. At other times, it is important to know the local mechanical properties, especially when the material is known to be inhomogeneous.

There are many well-established approaches for determining the mechanical properties of materials. With an assumption of homogeneity, bulk mechanical properties can be determined from measurements of overall loads and deflections imparted to a sample of the material. Another approach for measuring certain mechanical properties is to apply a known pressure to the surface of a material and measure the resulting deformation at the surface. This is a common method for measuring the hardness of metals.

For soft, or low modulus, materials (e.g., certain plastics, foams, biological soft tissues), referred to here as deformable materials, it is sometimes inconvenient or impossible to grasp the bulk material for the purpose of imparting loads or deformations. It is also sometimes desirable to make measurements without directly touching the material with instruments. In-vivo measurement of soft tissue properties is such a case where removing material for testing, or contacting the tissue with instruments, can be injurious.

In addition to measuring bulk material properties in deformable materials, it is sometimes desirable to locate and characterize highly localized inhomogeneities or anomalies within the bulk material. For example, there may be a flaw in the material that is markedly harder or softer than the surrounding material. In the case of biological soft tissues, a locally diseased area (e.g., a cancerous nodule) is often harder than the healthy tissue around it. Indeed, the localized differences in mechanical properties of healthy and diseased tissue form the basis of the centuries-old practice of palpating (i.e., touching and manipulating) tissue to diagnose and treat patients.

A particularly challenging situation in medicine is measuring in-vivo tissue mechanical properties during minimally invasive surgery (MIS) such as laparoscopy, arthroscopy, and thoracoscopy. In MIS, the surgeon accesses and views the target anatomy through small incisions using long, small-diameter instruments and optics. It is difficult or impossible to directly palpate tissues with the fingers, making it necessary to use specially designed instruments to gain an understanding of tissue mechanical properties and to search for anomalies in the tissue. In one type of MIS, thoracoscopic surgeons remove small cancerous nodules from lung tissue that have been identified using CT scans. However, if the target nodule is below the surface of the lung, locating it can be very difficult using standard MIS instruments.

Approaches for measuring bulk and local material properties of biological soft tissues, and for locating and differentiating diseased from healthy areas of tissue, include use of sonic and ultrasonic wave propagation in tissue. These approaches are not optimal, especially for use in MIS applications, either because the apparatus is too large to conveniently be deployed through small openings or because the instrument must directly contact the tissue in order to make the measurement. In addition, these approaches are often time consuming to carry out, making them impractical for use during surgery.

SUMMARY OF THE INVENTION

In view of the foregoing, embodiments according to aspects of the present invention non-destructively measure the bulk mechanical properties of deformable materials, both man-made and natural.

In addition, embodiments non-destructively locate and characterize local inhomogeneities in mechanical properties at, or just below, the surface of deformable materials.

In particular, some embodiments non-destructively measure the mechanical properties of biological soft tissues during minimally invasive surgery and locate anomalies that may indicate disease.

In some embodiments, the measurements are performed without directly contacting the material being tested. The measurements are also performed very quickly and with minimal operator manipulation.

According to aspects of the present invention, embodiments deform the surface of the material with a probe, such as a mechanical device or a gas/liquid jet, while optically recording in detail the three-dimensional (3D) topography of the resulting surface deformation. The probe effectively applies a forcing function to the material, the attributes of which are known by performing calibrations prior to use or by direct measurement while it is applied. The topography is effectively the system output that is measured as indicative of the underlying mechanical properties of the material. In a particular application, embodiments apply a pressure in-vivo to human tissue and analyze a three-dimensional topography of the resulting surface deformation to identify localized inhomogeneities and anomalies in the human tissue.

DETAILED DESCRIPTION

According to aspects of the present invention, a device for imparting a deforming pressure to the surface of the material (a probe) is used in combination with 3D topography acquisition to measure the resulting deformation in the surface. Information from the probe and the topography system is used to compute the bulk mechanical properties of, and anomalies within, the material using appropriate mathematical and materials models. For simplicity here, bulk mechanical properties and anomalies in those properties, along with dimensions and shapes of surface features, will together be termed properties of the material.

Figure 1:
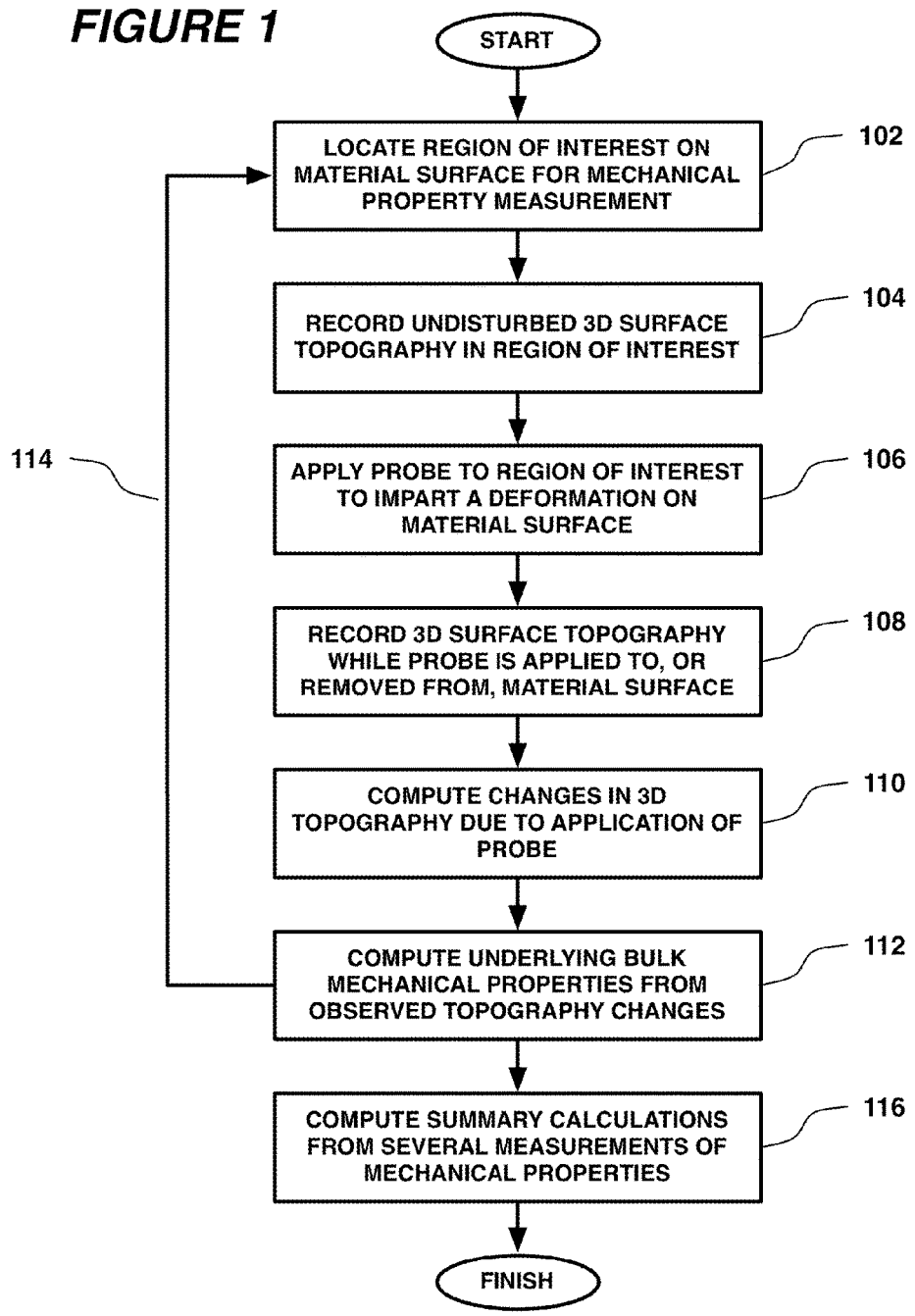
FIG. 1 is a block diagram of the steps for determining the bulk mechanical properties of a deformable material, according to aspects of the present invention.

FIG. 1 details the steps in an example embodiment for measuring the bulk mechanical properties of a deformable material. In step 102, a region of interest (ROI) on the surface of the material of interest is located. It is not in general necessary to remove the material from its setting into an apparatus. As such, the embodiment provides a non-destructive approach for making measurements of the material. This is particularly advantageous for in-vivo measurements of soft tissue. In step 104, an initial measurement of the 3D topography in the undisturbed ROI is made. This baseline topography can be used in subsequent calculations. In step 106 the probe is applied to the surface to impart a controlled deformation. As the probe is applied to, or removed from, the material surface, 3D topographic data are acquired in step 108. In step 110, the data acquired in steps 104 and 108 together are used to compute changes in the 3D topography resulting from application of the probe to the material surface. The results provide an approach in step 112 for computing bulk mechanical properties. These steps may be repeated one or more times to allow computation of, for example, an average over several readings in steps 114 and 116.

Figure 2:
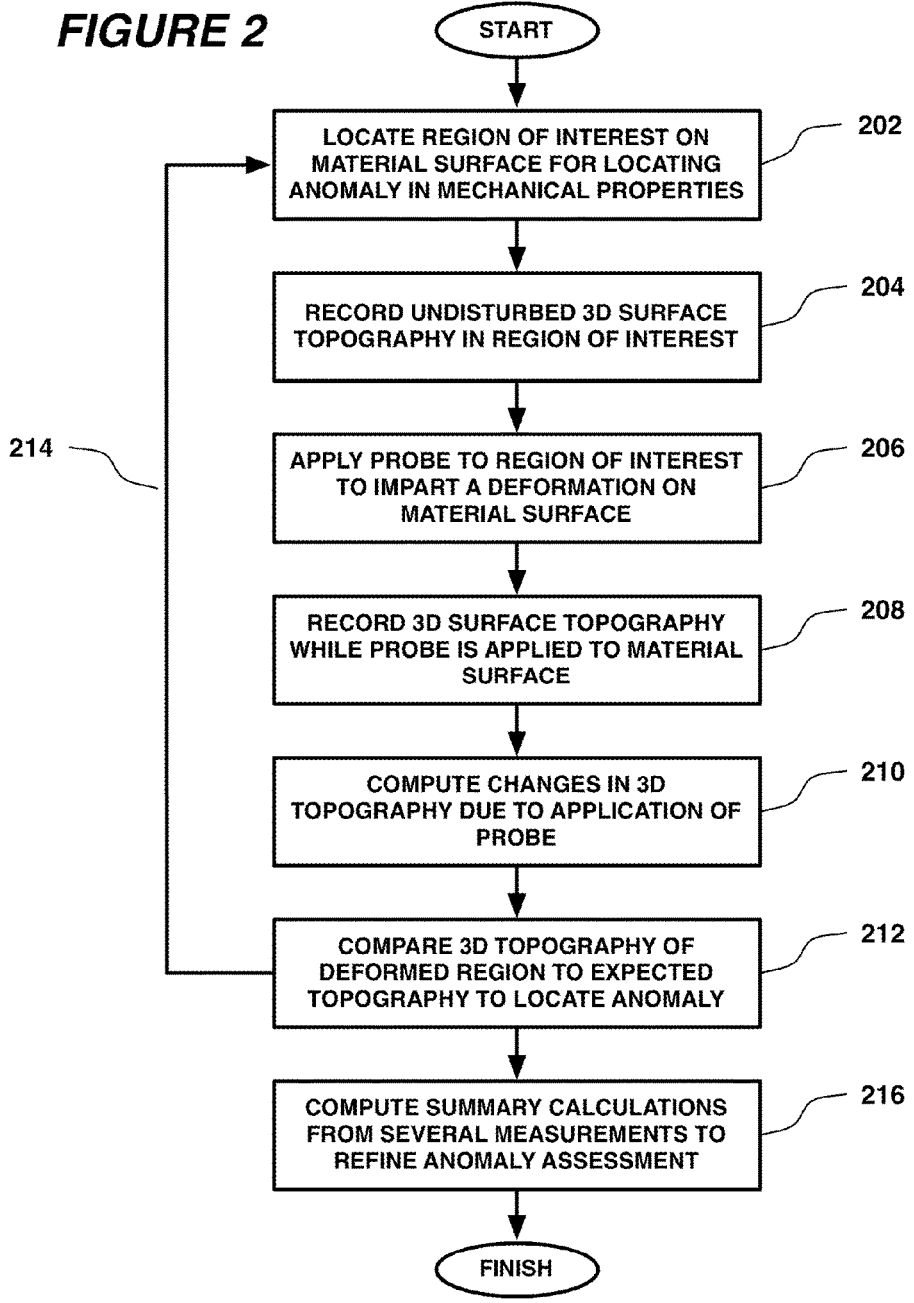
FIG. 2 is a block diagram of the steps for locating an anomaly in the mechanical properties of a deformable material, according to aspects of the present invention.

FIG. 2 details the steps in another example embodiment for measuring the bulk mechanical properties of a deformable material. In step 202, a region of interest (ROI) on the surface of the material of interest is located. In step 204, an initial measurement of the 3D topography in the undisturbed ROI is made. This baseline topography can be used in subsequent calculations. In step 206, the probe is applied to the surface to impart a controlled deformation. As the probe is applied to, or removed from, the material surface, 3D topographic data are acquired in step 208. In step 210, the data acquired in steps 204 and 208 together are used to compute changes in the 3D topography resulting from application of the probe to the material surface. By comparing the resulting topography against an expected (or "canonical") topography in step 212 for a certain type of imparted probe pressure, it is possible to discern the presence of an anomaly in the material. These steps may be repeated one or more times to allow computation of, for example, an average over several readings in steps 214 and 216.

Figure 3:
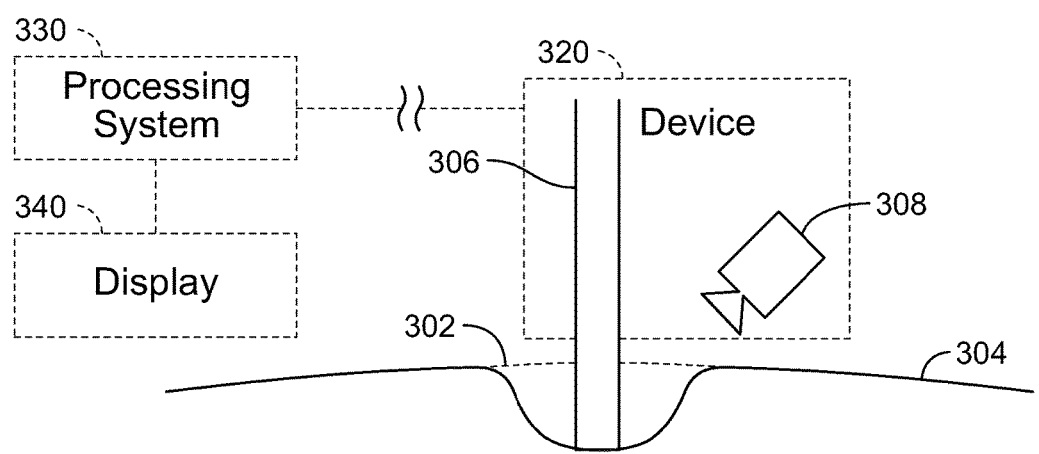
FIG. 3 shows in cross-section the topography of a deformable material during the application of a rigid or flexible probe to the surface of the material, according to aspects of the present invention.

FIG. 3 shows a schematic of the deformation of a material surface from its original undisturbed shape 302 to a deformed shape 304 when a probe 306 directly contacts the surface of the material. A system for recording the 3D topography 308 is positioned so as to record changes in the surface.

Figure 4:
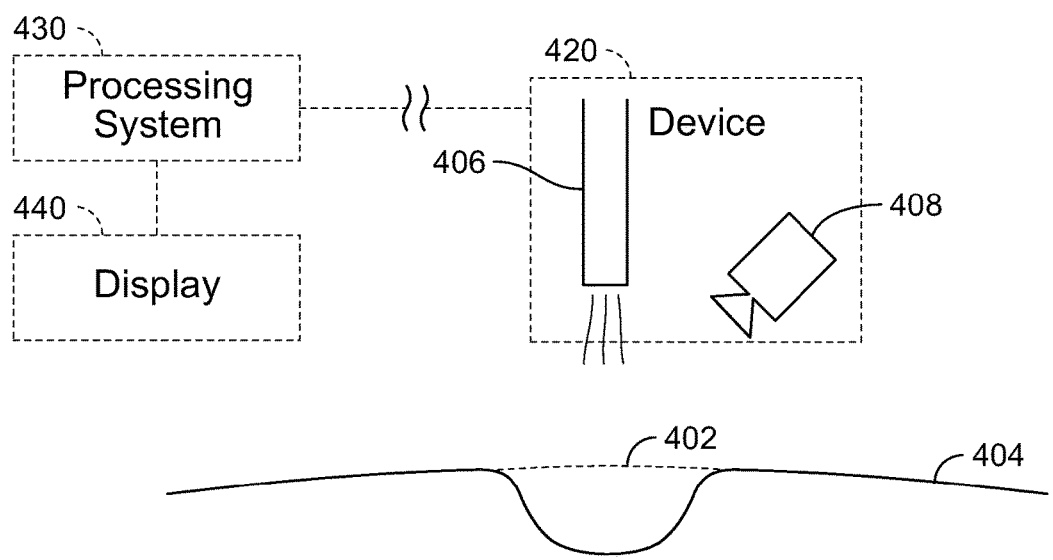
FIG. 4 shows in cross-section the topography of a deformable material during the application of a gas or liquid jet probe, according to aspects of the present invention.

FIG. 4 shows a schematic of the deformation of a material surface from its original undisturbed shape 402 to a deformed shape 404 when a probe 406 applies a pressure to the surface using a gas/liquid stream. A system for recording the 3D topography 408 is positioned so as to record changes in the surface.

Figure 5:
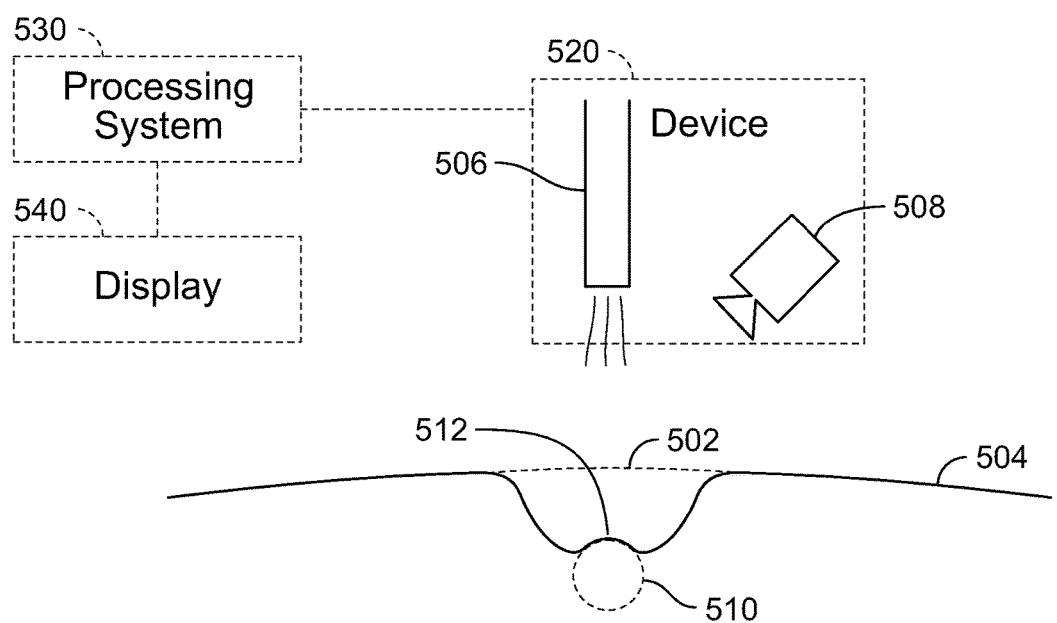
FIG. 5 shows in cross-section the topography of a deformable material with a localized anomaly during the application of a gas or liquid jet as the probe, according to aspects of the present invention.

FIG. 5 shows a schematic of the deformation of a material surface from its original undisturbed shape 502 to a deformed shape 504 when a probe 506 applies a pressure to the surface using a gas/liquid stream. In the case shown, an anomaly 510 is present below the surface of the material. The anomaly 510 creates a distinguishable feature 512 on the surface of the deformation. A system for recording the 3D topography 508 is positioned so as to record changes in the surface.

In a further embodiment, the probe is a rigid or flexible device that can be pushed into the material surface (306). The device, especially for use in confined spaces such as minimally invasive surgery, may be a long, thin rod. In other uses, the device may be a take on any convenient shape. The device may incorporate force-sensing elements (e.g., a strain gage, capacitive, optical or other force-sensitive transducer) so that the mechanical load imparted to the material can be measured. The device may also incorporate a position sensor that records the degree to which the rod has been pushed into the material. The device may also incorporate a sensor that determines its position relative to the 3D topography recording system. In yet another embodiment, the device incorporates a grasping tip. The device can then be used to deform the material surface by pulling it outward. In another embodiment, the device incorporates means to pinch or stretch the material in the plane of the surface.

In a further embodiment, the probe is a stream of gas or liquid that is directed at, and deforms, the material surface 406 and 506. The distribution of load across the surface may be non-uniform (e.g., the pressure distribution of the gas stream at the surface may be shaped like a bell curve). In a particular embodiment, the nozzle that produces the gas or liquid stream has a circular cross section that creates a cylindrical or conical stream. In another embodiment, the nozzle outlet is flattened to generate a planar stream to create a different deformed surface topography. In yet another embodiment, the nozzle is annular to create a different deformed surface topography. In a further embodiment, the stream is drawn into the probe to create negative pressure near the material surface, causing a bulge rather than an indentation. In a further embodiment, the stream is moved across the material surface in a defined manner to deform a larger area. In another embodiment, an auxiliary device is used in advance to calibrate and characterize the pressure distribution created by the gas or liquid stream as a function of the driving pressure, velocity, distance, and shape of the stream. This information can be combined with measurements of the material surface deformations to achieve a more detailed analysis of the mechanical properties.

In a further embodiment, the probe and the topographic system are integrated into a single device. Such option is schematically represented, via dash line, in each of the afore-mentioned FIGS. 3-5 as items 320, 420 and 520, respectively. This is particularly advantageous when measurements are taken in confined spaces, such as in minimally invasive surgery. One such embodiment places the rigid probe or the gas/liquid stream delivery channel directly alongside the optics of the topographic system. In another embodiment, the gas/liquid stream delivery channel is an annulus around and co-axial with the optics of the topographic system. Such parallel or co-axial arrangements produce an advantageous viewing angle of the resulting deformation.

In another embodiment, the probe is applied to the material surface not at a single point but at more than one point, either simultaneously or in a temporal pattern. One such pattern sweeps the probe across the material surface in a painting or raster-scan fashion. In so doing, larger areas of the material can be probed while the resulting deformations are monitored or recorded with the topographic system. This approach may be especially useful in rapidly locating zones in the material with different mechanical properties (e.g., nodules in soft tissue).

In another embodiment, the probe is applied to the material surface in a defined, time-varying fashion, including but not limited to (a) cyclic waveforms of one or multiple combined frequencies (e.g., sine waves, "chirps," broad spectrum, and the like), (b) delta functions, and (c) non-cyclic waveforms (e.g., white noise). Such time-varying applied loads allow certain dynamic mechanical properties (e.g., damping coefficients, viscoelasticity) of the material to be measured.

According to aspects of the present invention, embodiments use true topographic data that faithfully captures the details of the contours and shape of the surface deformation. That is, it is not sufficient that stereoscopic views of the deformation be presented to a human observer as a 3D visual effect. It is instead necessary to have a grid of (x, y, z) coordinate points closely enough spaced across the material surface that an accurate spatial model of the deformation can be computed and analyzed. It is also particularly advantageous to acquire the topographic data at a sufficiently high speed to capture real time changes in topography as the surface is deformed and subsequently returns to its normal shape.

Several approaches may be employed to measure 3D surface topographies (e.g., stereoscopic, time-of-flight, laser triangulation, interferometry, photogrammetry, and structured lighting). A particular approach for measuring surface deformations of soft materials is spatial phase imaging (SPI). As such the above-mentioned system for recording the 3D topography 308/408/508 (see FIGS. 3-5, respectively) can include SPI. This technology is described in U.S. Pat. Nos. 5,557,261; 5,890,095; 6,671,390; and 6,810,141 all to Barbour, and in U.S. Patent Application Publication No's 2002/0181761 and 2005/0163365 both to Barbour, the contents of these patents and patent applications being incorporated entirely herein by reference. SPI is an optoelectronic technology that directly measures 3D topographies of reflective surfaces with high accuracy and at high speed. The technology can collect real-time 3D video that permits measurement of temporal changes in topography. The data from this device can be analyzed to yield detailed information about the shape, surface, and texture of three-dimensional reflective surfaces. SPI technology allows a unique combination of important performance attributes to be incorporated in the system, including compact form factor, high spatial resolution, high-speed data acquisition, and ability to acquire data through a single-aperture optic.

For the topographic system, special types of incident lighting improve the performance of the sensor that acquires topographic data. In one embodiment, two or more light sources illuminate the material from different positions relative to the optics of the topographic system. In another embodiment, the light has been polarized in particular directions. In yet another embodiment, the light emanates from a diffuse source, a specular source, or a combination of diffuse and specular sources. In yet another embodiment, the light has broad-spectrum wavelength content or selected spectrum wavelength content. This embodiment is particularly advantageous for measuring biological soft tissues whose reflective properties depend upon the incident wavelength of light.

In one embodiment, one or more single-shot topographic images are acquired in synchrony with certain aspects of the deforming probe. In another embodiment, a video stream of topographic images is acquired while the probe deforms the material surface. The images are analyzed either during or after the measurement to determine the degree to which the material was deformed when loaded. In one embodiment, 3D images or video are acquired after the probe is removed from the material. The changes in surface shape recorded over time in this fashion allow viscoelastic properties of the material to be measured.

In another embodiment, 3D topographic images are recorded from the material surface at a place that is remote from the site of application of the probe. This permits measurement of the degree to which deformations propagate through the material, providing another means of determining the underlying mechanical properties of the material.

The invention performs calculations on the topographic data to determine bulk mechanical properties. When used in conjunction with a direct contact probe, one embodiment calculates the depth of the deformation from the 3D topography. This is advantageous to the probe design, as it would not need an independent means for determining its tip position relative to the material surface. In this embodiment, the (x, y, z) coordinates for points across the surface, and into the deformation area, can be used to directly compute the depth of the deformation. Combined with a measurement of the force applied to the material by the probe, the bulk mechanical properties at that site can be computed. In another embodiment of the analysis, local measures of surface curvature is used to determine mechanical properties. Computing curvatures of the deformed surface in varying directions provides a measure of directional anisotropy in mechanical properties. In the case of an indentation caused by a mechanical device or a gas/liquid jet, differences in curvature measured along orthogonal axes may indicate an anisotropy in the mechanical properties. This provides a means, for example, of determining the orientation of collagen fibers in tissues such as skin. In another embodiment, a 3D topographic measurement is made of the material surface prior to application of a deforming pressure. The z-coordinates of this initial-condition topography are subtracted on a point-for-point basis across all (x, y) points of the deformed topography to yield a net topography that can be ascribed strictly to the effect of the applied deforming pressure.

For the case in which the topographic system measures surface topography at a location remote from the site of probe's deforming pressure, one embodiment of the calculation is to measure the time between the application of the pressure and the appearance of a propagating surface deformation at the remote site. Another embodiment is to measure the specific geometric attributes (e.g., deformation height, deformation width) of the propagating surface deformation at the remote site. Yet another embodiment is to feed back to the probe controller certain information from the remote measurement site to modulate the probe's deforming pressure.

To accomplish the purpose of locating anomalies, a different style of calculations is performed. Essentially, 3D surface images are analyzed mathematically to identify or extract topographic features that are indicative of an underlying inhomogeneity. The analysis begins by measuring or constructing a canonical smooth topography that would result from deforming a completely homogeneous sample of the material being tested. An embodiment of this analysis is to fully characterize the 3D deformation, including maximum displacement, overall extent or diameter, curvatures in one or more directions, and surface textures. A next step is to deform an area suspected of having anomalies and record the 3D deformation in that area. If an anomaly is present, it creates a local variation in the topography. The topography of the test area is compared to the canonical smooth topography to reveal the location of the underlying anomaly. An embodiment of this analysis is to perform a point-for-point subtraction of the z-coordinates of the canonical topography from the test topography across all (x, y) points in the two topographies and identify discrepancies that are due to the underlying anomaly. Another embodiment of this analysis is to compare local surface curvatures across all (x, y) points in the two topographies and identify discrepancies that are due to the underlying anomaly. In another embodiment of this analysis, spatial frequencies are compared across the two topographies to identify discrepancies that are due to the underlying anomaly.

In another embodiment of the analysis, frame-from-frame subtraction is used to highlight changes in the topography as the deforming means is advanced into or swept across the material surface.

In another embodiment of the analysis, measurements of changes in surface topography is coupled with finite element analysis (FEA) to build a better understanding of the mechanical properties or performance of the material.

Images from the topographic system and results from the subsequent analyses are presented to the user of the apparatus via a display (such is schematically represented, via dash line, in each of the afore-mentioned FIGS. 3-5 as items 340, 440 and 540, respectively). There are different designs and types of displays that can be incorporated in the system. In one embodiment, a conventional two-dimensional display (e.g., a computer monitor or television monitor) is used. In another embodiment, a stereoscopic display is used. Examples of stereoscopic displays include, but are not limited to, stereoscopic displays that do not require the user to wear special goggles, and interlaced displays that require the user to wear special goggles that separate images for the left and right eyes (e.g., polarizing lenses, shuttered lenses, and the like). In another embodiment, a volumetric display (e.g. holographic) is used.

In addition, there are different approaches to displaying the information to the user that are particularly advantageous to understanding the results. Since the information gathered from the topographic system, and the analyses performed, are inherently three-dimensional, it is possible to present to the user as-seen, hyper-realistic, and otherwise enhanced representations of the 3D information that synthesize depth cues (e.g., parallax, occlusion, shadows, lighting). In one embodiment, the user controls using software the virtual camera angle from which the topography or analysis are viewed. In another embodiment, the user controls using software the virtual illumination angle of the topography or analysis results. In so doing, virtual shadows are created across the topography or analyses. Both of the foregoing embodiments are advantageous because they create for the user additional depth cues that aid in the notional understanding of shapes and textures.

In addition to measuring mechanical bulk properties of deformable materials and locating anomalies within them, and with particular reference to applications in medicine, the present invention has utility in making other important measurements in-vivo. By imparting a deforming pressure to a tissue surface while recording the resulting changes in topography with 3D SPI, these in-vivo measurements include, but are not limited to, (a) measuring the pressure inside a vessel or hollow organ, (b) assessing aneurysm rupture risk by measuring the wall thickness or stiffness of the aneurismal sac, (c) measuring the nature or integrity of interfaces between man-made implants (e.g., sutures, closure devices, ports, bands, fabrics, stents, and the like) and neighboring tissues, and (d) measuring the nature or integrity of interfaces between biological materials (e.g., grafts, transplants, and the like) and neighboring tissues. Because spatial phase images can be acquired through standard optics, it is possible to obtain surface topography data through existing small-bore optical devices that can be inserted into confined areas. Such devices include boroscopes and medical endoscopes. The latter general category of devices can be further detailed to include arthroscopes, laparoscopes, thoracoscopes, cystoscopes, colonoscopes, hysteroscopes, laryngoscopes, rhinoscopes, and the like. As mentioned above, the probe and the topographic system can be integrated into a single device. Also as mentioned above, such is particularly advantageous when measurements are taken in confined spaces, such as in minimally invasive surgery. For such surgery, the integration for work in confined spaces can be the above-mentioned medical endoscope.

With particular reference to the challenges posed by having to make these measurements or locate anomalies during minimally invasive surgery, there are certain characteristics of systems and methods that are especially important. The devices employed must be small enough to be inserted through typical MIS incisions, and compact and low mass enough to be easily manipulated by hand. The mechanical interaction of the devices with tissue must be atraumatic. The acquisition of data must be rapid so as (i) to minimize exposure of the tissue to probing, (ii) to reduce measurement artifacts that stem from movement of the tissue and instruments, and (iii) to avoid extending the overall procedure time to accommodate the added measurements. Finally, the system used to acquire the 3D topographic data from the tissue surface must have sufficiently high spatial resolution and accuracy to capture potentially subtle differences in surface contours that result from the underlying bulk mechanical properties or the presence of anomalies in the tissue.

In addition to its applications to analysis of deformable materials, the invention can be used advantageously to perform non-destructive testing (NDT) of rigid materials. In one embodiment, the probe incorporates a vibration inducing actuator that is used to excite a material such as a composites, metals, and plastics. The actuator signal is swept through a range of mechanical frequencies while a spatial phase imaging (SPI) camera captures the topography of the material surface. The processing system is used to detect cracks, dimensional variations, hardness variations, delaminations, material property variations, coating abnormalities and missing features, all of which affect topography at various excitation frequencies. The SPI camera is particularly well suited to NDT surface inspection because it is fast, high resolution, compact, low cost and directly measures normal vectors that change rapidly and systematically in the vicinity of anomalies.

The embodiments described herein may employ a processing system (such is schematically represented, via dash line, in each of the afore-mentioned FIGS. 3-5 as items 330, 430 and 530, respectively) to control aspects of the present invention or to perform calculations/computations according to aspects of the present invention. Generally, the processing system may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium. The processing system may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments, as is appreciated by those skilled in the computer and software arts. The physical processors and/or machines may be externally networked with other devices of the embodiments, or may be integrated with these devices to reside within the same housing. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software. Stored on any one or on a combination of computer readable media, the exemplary embodiments may include software for controlling the devices and subsystems of the exemplary embodiments, for driving the devices and subsystems of the exemplary embodiments, for enabling the devices and subsystems of the exemplary embodiments to interact with a human user, for performing calculations/computations, and the like. Such software can include, but is not limited to, device drivers, firmware, operating systems, development tools, applications software, and the like. Such computer readable media further can include the computer program product of an embodiment for performing all or a portion (if processing is distributed) of the processing performed in implementations. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like. Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention. It is further understood that embodiments may include any combination of the features and aspects described herein.

What is claimed is:

1. An endoscopic system for determining a property of human tissue, comprising:
    a probe comprising a portion delivering a stream of gas that applies a pressure to a surface of the human tissue and deforms an area of the surface;
    a spatial phase imaging sensor that uses spatial phase image information and that measures three-dimensional surface topographies of the area of the surface of the human tissue including three-dimensional surface topographies of the deformation of the area of the surface in response to the application of the pressure by the probe;
    a processing system that receives the three-dimensional surface topographies from the spatial phase imaging sensor and determines a property of the human tissue from the three-dimensional surface topographies; and
    a display system that displays information relating to a property of the human tissue.

2. The system of claim 1, further comprising one or more sensors that determine the pressure applied by the probe, the processing system determining a property of the deformable material from the plurality of three-dimensional surface topographies and the pressure determined by the one or more sensors.

3. The system of claim 1, wherein the probe includes a nozzle that applies a stream of gas or liquid to the surface of the material.

4. The system of claim 1, wherein the probe moves the applied pressure across the surface of the material.

5. The system of claim 1, wherein the probe applies the pressure to the more than one area on the surface of the material according to a temporal pattern.

6. The system of claim 1, wherein a measurement of the position of the probe relative to the material surface is made.

7. The system of claim 1, wherein the processing system further receives a measurement of a position of the probe relative to the topographic system to determine the property of the deformable material.

8. The system of claim 1, wherein the probe applies the pressure to the surface of the material according to a waveform.

9. The system of claim 1, wherein the topographic system includes a stereoscopic sensor, time-of-flight sensor, laser triangulation sensor, interferometric sensor, photogrammetric sensor, or structured light sensor.

10. The system of claim 1, wherein the topographic system determines the three-dimensional surface topography at a location on the surface of the material that is different from where the probe applies the pressure.

11. The system of claim 1, wherein the topographic system determines the three-dimensional topography at a plurality of moments in time.

12. The system of claim 1, wherein the display system displays three-dimensional depth cues computed from the topographic analysis.

13. A method for determining a property of a human tissue using and endoscopic system, the method comprising:
    applying a pressure by a stream of gas to a surface of the human tissue with a probe that comprises a portion for delivering the stream of gas such that an area of the surface of the human tissue is deformed;
    measuring, with a spatial phase imaging sensor that uses spatial phase image information, three-dimensional surface topographies of the area of the surface of the human tissue including three-dimensional surface topographies of the deformation of the area of the surface in response to the application of the pressure by the probe;
    determining a property of the human tissue according to the three-dimensional surface topographies;
    displaying, on a display, information relating to the property of the human tissue; and
    determining a treatment for the human tissue based on the information displayed on the display.

14. The method of claim 13, further comprising determining the pressure applied by the probe with one or more sensors, wherein the property of the human tissue is determined from the plurality of three-dimensional surface topographies and the pressure determined by the one or more sensors.

15. The method of claim 13, further comprising, before applying the pressure to the surface of the human tissue, determining, with the topographic system, an initial three-dimensional surface topography of the surface of the human tissue.

16. The method of claim 13, wherein applying the pressure to the human tissue includes applying a stream of gas or liquid to the human tissue to deform the human tissue in-vivo, determining the property of the human tissue includes identifying localized anomalies in the human tissue, and determining the treatment includes determining a treatment forte localized anomalies.

* * * * *

UNITED STATES PATENT AND TRADEMARK OFFICE
CERTIFICATE OF CORRECTION

PATENT NO. : 9,693,728 B2
APPLICATION NO. : 13/172787
DATED : July 4, 2017
INVENTOR(S) : Harry et al.

It is certified that error appears in the above-identified patent and that said Letters Patent is hereby corrected as shown below:

In the Claims

Column 12, Line 22, please delete "forte" and insert therefor --for the--

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*